United States Patent [19]

Bass

[11] Patent Number: 4,752,222

[45] Date of Patent: Jun. 21, 1988

[54] ORTHODONTIC APPLIANCE

[76] Inventor: Neville M. Bass, 4 Queen Anne St., London, W1M 9LE, Isle of Man

[21] Appl. No.: 941,403

[22] Filed: Dec. 15, 1986

[30] Foreign Application Priority Data

Jul. 7, 1986 [GB] United Kingdom ............... 8616499
Jul. 17, 1986 [GB] United Kingdom ............... 8617521
Jul. 29, 1986 [GB] United Kingdom ............... 8618403

[51] Int. Cl.$^4$ .............................................. A61C 3/00
[52] U.S. Cl. .......................................... 433/7; 433/6
[58] Field of Search ................................. 433/7, 6

[56] References Cited

U.S. PATENT DOCUMENTS

| | | | |
|---|---|---|---|
| 4,239,487 | 12/1980 | Murdock | 433/7 |
| 4,416,626 | 11/1983 | Bellavia | 433/7 |
| 4,431,411 | 2/1984 | Witzig et al. | 433/6 |
| 4,433,956 | 2/1984 | Witzig | 433/7 |
| 4,637,796 | 1/1987 | Korn | 433/7 |

FOREIGN PATENT DOCUMENTS

| | | | |
|---|---|---|---|
| 3241105 | 5/1984 | Fed. Rep. of Germany | 433/7 |
| 1020995 | 2/1953 | France | 433/7 |

*Primary Examiner*—John J. Wilson
*Attorney, Agent, or Firm*—Andrus, Sceales, Starke & Sawall

[57] ABSTRACT

An orthopedic modular assembly and an orthodontic appliance employing two similar assemblies are disclosed. Each modular assembly includes a housing component of stainless steel or synthetic plastics material comprising two pairs of parallel passages extending at right angles to one another and providing bores for the slidable mounting of a lingual pad support and a side screen support respectively. The appliance is assembled from two modular assemblies which are maintained in position on the left-and right-hand sides of the appliance by a synthetic plastics former and adjustably support pairs of lingual pads, side screens and other components as required.

13 Claims, 2 Drawing Sheets

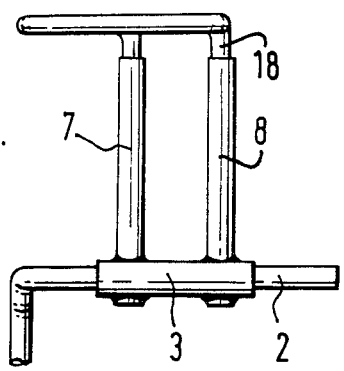
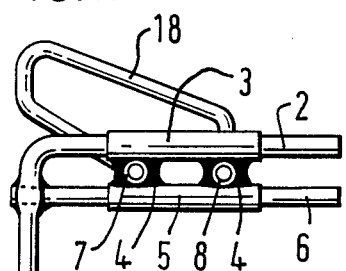
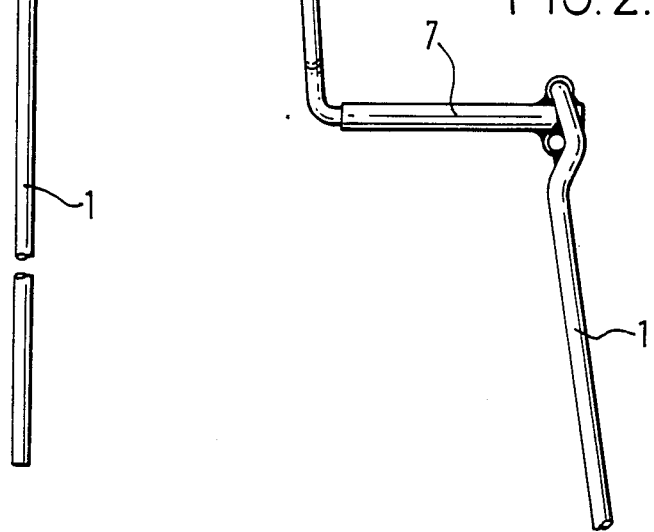
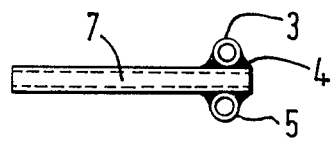

4,752,222

ORTHODONTIC APPLIANCE

BACKGROUND AND SUMMARY OF THE INVENTION

This invention relates to an orthopedic modular assembly for application to one side of a patient's mouth and to a dento-facial orthodontic applicance comprising two such assemblies.

It is one object of the invention to provide a modular assembly comprising a pre-formed housing components which forms a fixed support for other adjustable or removable components of the assembly.

It is another object of the invention to provide two modular assemblies deformable and adjustable to fit opposite sides of a patient's mouth and slidably connectable to the housing assemblies to form an orthodontic appliance which can be modified as treatment proceeds.

It is a further object of the invention to provide an orthodontic appliance which can be readily assembled with preferred components to suit the requirements of a particular patient and is adjustable after assembly to suit the changing requirements of an individual patient, consequent upon the continuing growth of the individual's jaw. It is a still further object of the invention to provide a new and improved orthodontic appliance capable of modifying the dento-facial development in a growing individual and more specifically, or correcting dental malocclusion and improving facial appearance resulting from a lack of forward growth of the mandible.

One or more of the aforesaid objects are achieved by the provision of an orthopedic modular assembly comprising a housing component of rigid material providing a first vertically spaced pair of parallel passages and a second horizontally spaced pair of parallel passages extending substantially at right angles to said first pair, a second component in the form of a lingual pad support having a pair of parallel arms adapted to form a snug sliding fit within said first pair of housing passages and a further arm extending substantially at right angles to said pair of arms and adapted to conform to the line of one side of a patient's mouth and a third component having a pair of parallel prongs adapted to fit within said second pair of housing passages and a portion extending upwardly at an angle to said prongs for supporting a member designed to act on the cheek at said one side of the patient's mouth.

One or more further objects of the invention are achieved by the provision of an orthodontic appliance comprising two modular assemblies adjusted to the shape of the left-and-right-hand sides respectively of a patient's mouth, a layer of synthetic plastics material formed to the shape of the patient's mouth and serving to fix said assemblies in position relative to one another and in correct relationship to the patient's mouth, and a plurality of components designed to act on selected parts of the patient's face and adjustably supported by said assemblies and said plastics layer.

BRIEF DESCRIPTION OF THE DRAWINGS

The invention will be described in greater detail hereinafter, with reference to the accompanying drawings in which:

FIG. 1 is a front view of a right-hand modular assembly in accordance with the invention;

FIG. 2 is a side view of the assembly of FIG. 1;

FIG. 3 is a plan view of the assembly;

FIG. 4 is an end view of the assembly looking from left to right in FIG. 3;

DESCRIPTION OF THE PREFERRED EMBODIMENT

Figure 5:
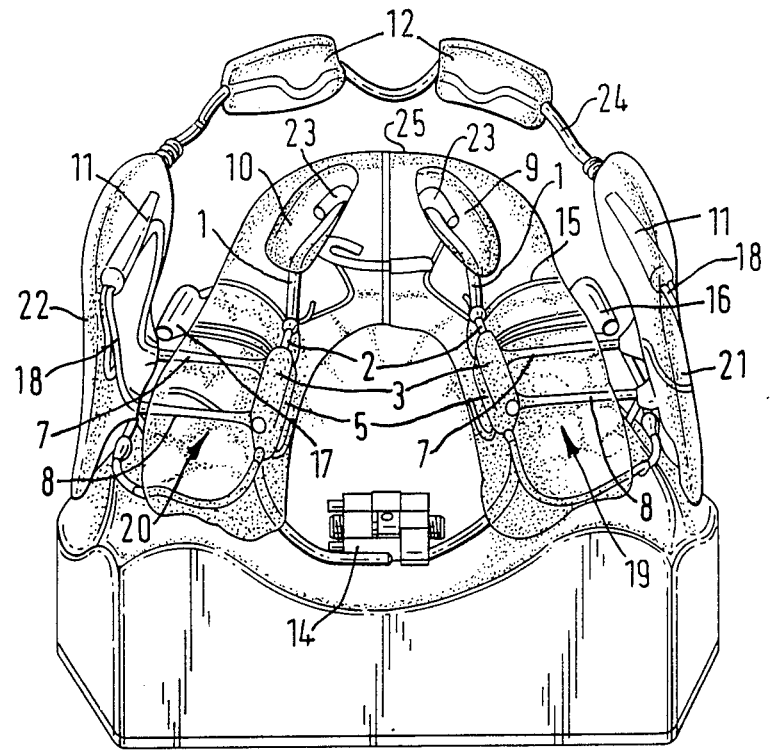
FIG. 5 is a rear perspective view of an orthodontic appliance in accordance with the invention designed for use in the upper part of a patient's mouth and incorporating two modular assemblies of the kind shown in FIGS. 1 to 4.
Figure 6:
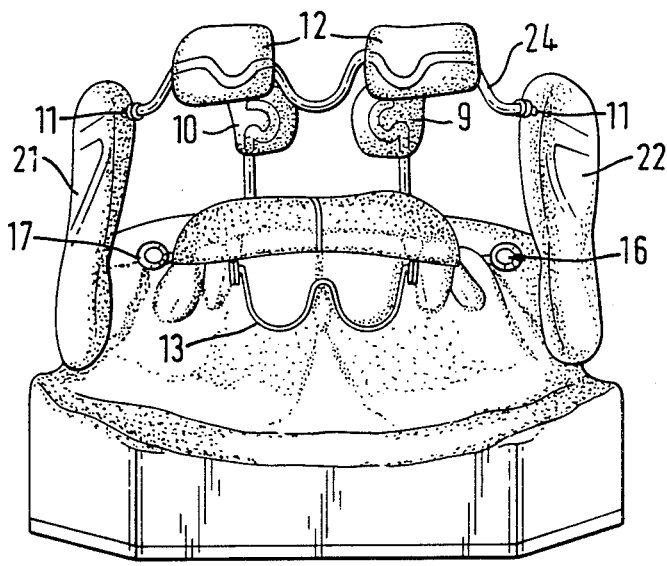
FIG. 6 is a front perspective view of the appliance shown in FIG. 5.

The right-hand assembly shown in FIGS. 1 to 4 is designed for use in combination with a left-hand assembly which is a mirror-image of itself, in the construction of the orthodontic appliance shown inverted and mounted on a shaped base in FIGS. 5 and 6.

This assembly includes a housing component comprising parallel tubes 3, 5 of stainless steel connected together by silver solder 4 which also serves to secure two further parallel tubes 7, 8, also of stainless steel which extend at right angles to the tubes 3, 5. Instead of soldered stainless steel the entire housing component may be in one piece or moulded from synthetic plastics material. The tubes 3, 5 form passages to slidably receive the parallel arms 2, 6 of a support 1, made of stainless steel wire, for a lingual pad 10 (FIG. 5). The tubes 7, 8 form passages to slidably receive parallel prongs on a member 18 of stainless steel wire. Synthetic plastics material may be added to form a side screen 22 (FIG. 5).

In constructing an orthodontic appliance of the kind shown in FIGS. 5 and 6 for use in the upper part of the mouth to correct dental malocclusion resulting from a lack of forward growth of the mandible in an individual patient, a right-hand modular assembly 20 of the kind illustrated in FIGS. 1 to 4 and a left-hand modular assembly 19 constructed as a mirror-image of the assembly 20 are arranged so that, in use, the tubes 7, 8 extend transversely of and beneath the upper back teeth of the patient and the member 18, arranged in the outer ends of the tubes, form slidable supports for a pair of detachable left-and-right-hand side screens 21 and 22 respectively, preformed from stainless steel or synthetic plastics material to act on the patient's cheeks. The components 1 of the assemblies 19, 20 are deformed to conform to the sides of the patient's mouth and support a pair of left-and-right-hand lingual pads 9, 10 in positions to stimulate forward posturing of the mandible in the individual patient, and the free ends of the arms are bent to form hooks 23 which enter blind bores in the pads. The slidable mounting of the arms 2, 6 in the tubes 3, 5 enables the pads 9, 10 to maintain stimulation by forward adjustment as jaw growth proceeds.

Each of the side screens 21, 22 is formed with a bore 11 to receive one end of an elongate support 24 formed from wire or synthetic plastics material, for a pair of pre-formed lip pads 12 formed from synthetic plastics material and designed to act on the lip muscles of the patient.

A preformed torque spring 13 is provided at the front of the appliance to control movement of the roots of the upper front teeth and to retain the appliance in place on the teeth. An expansion screw 14 whereby the appliance can be adjusted in width is attached to the central portion of the appliance. The modular assemblies 19, 20 are embedded in a plastics former 25 which follows the lines of the teeth and also carries mountings 15 for a pair of sockets 16, 17 which are adapted to receive the inner ends of a demountable face bow (not shown) designed to allow applications of force from outside the mouth.

I claim:

1. For use in an orthodontic appliance, an orthopedic modular assembly for securement in place on one side of the appliance, said assembly comprising, in combination:
   (a) a rigid housing component having a first pair of parallel tubes (3, 5) connected together in vertically spaced relation, and further having a second pair of parallel tubes (7, 8) disposed in horizontally spaced relation and with said second pair of tubes extending from one side of said first pair and disposed at substantially right angles to the latter,
   (b) a lingual pad support having a pair of vertically spaced parallel arms (2, 6) adjustably slidingly disposed within said first pair of tubes, and further having a single arm (1) extending laterally from said pair of arms, and with said single arm having means (23) disposed at its outer end for removably receiving a lingual pad for stimulating growth of a user's jaw,
   (c) and a user's cheek side screen support (18) having a pair of horizontally spaced parallel members adjustably slidingly disposed within said second pair of tubes.

2. The modular assembly of claim 1 in which said housing component is constructed of synthetic plastic.

3. The modular assembly of claim 1 in which said housing component is constructed of stainless steel.

4. The modular assembly of claim 1 in which said lingual pad support is constructed of thin, elongate material.

5. The modular assembly of claim 4 in which said lingual pad support is constructed of stainless steel.

6. An orthodontic appliance comprising, in combination:
   (a) a synthetic plastic shaped base (25) formed to the contours of the upper portion of a user's mouth,
   (b) and a pair of left-and-right-hand modular assemblies secured to the lower portion of said base, each of said assemblies including:
      (1) a rigid housing component having a first pair of parallel tubes (3, 5) connected together in vertically spaced relation, and further having a second pair of parallel tubes (7, 8) disposed in horizontally spaced relation and with said second pair of tubes extending from one side of said first pair and disposed at substantially right angles to the latter,
      (2) a lingual pad support having a pair of vertically spaced parallel arms (2, 6) adjustably slidingly disposed within said first pair of tubes, and further having a single arm (1) extending laterally from said pair of arms, and with said single arm having means (23) disposed at its outer end for removably receiving a lingual pad for stimulating growth of a user's jaw,
      (3) and a user's cheek side screen support (18) having a pair of horizontally spaced parallel members adjustably slidingly disposed within said second pair of tubes.

7. The appliance of claim 6 which includes stainless steel side screens (21, 22) removably attached to said side screen supports (18) of said modular assemblies.

8. The appliance of claim 6 which includes synthetic plastic side screens (21, 22) removably attached to said side screen supports (18) of said modular assemblies.

9. The appliance of claim 6 in which the lingual pad supports of said modular assemblies are, in use, adjustable forwardly in the user's mouth relative to said housing components as jaw growth proceeds.

10. The appliance of claim 6 in which said second pair of tubes (7, 8) on said pair of assemblies extend, in use, transversely of and beneath the user's back teeth.

11. The appliance of claim 6 which includes:
    (a) side screens (21, 22) removably attached to said side screen supports (18) of said modular assemblies,
    (b) an elongate support (24) extending across said base (25) and connected to said side screens,
    (c) and a plurality of horizontally spaced lip pads (12) mounted on said last-named support.

12. The appliance of claim 6 which includes:
    (a) a torque spring (13) extending across and connected to said base (25),
    (b) said torque spring providing:
       (1) means for controlling movement of the roots of the user's upper front teeth,
       (2) and means for retaining the appliance in the user's mouth.

13. The appliance of claim 6 which includes expansion screw means (14) connected to and centrally located between said pair of modular assemblies for adjusting the width of the said appliance.

* * * * *

UNITED STATES PATENT AND TRADEMARK OFFICE
CERTIFICATE OF CORRECTION

PATENT NO. : 4,752,222

DATED : June 21, 1988

INVENTOR(S) : Neville M. Bass

It is certified that error appears in the above-identified patent and that said Letters Patent is hereby corrected as shown below:

On the cover page at [76], please change the inventor's address from "Isle of Man" to -- England --.

Signed and Sealed this

Eighth Day of March, 1994

BRUCE LEHMAN

Attest:

Attesting Officer

Commissioner of Patents and Trademarks